(12) United States Patent
Takashimizu

(10) Patent No.: US 9,429,512 B2
(45) Date of Patent: Aug. 30, 2016

(54) MICROCHIP, LIQUID SAMPLE SUPPLY DEVICE, SUPPLY METHOD OF LIQUID SAMPLE, AND ANALYSIS DEVICE

(75) Inventor: Toru Takashimizu, Kanagawa (JP)

(73) Assignee: Sony Corporation, Tokyo (JP)

( * ) Notice: Subject to any disclaimer, the term of this patent is extended or adjusted under 35 U.S.C. 154(b) by 878 days.

(21) Appl. No.: 13/402,209

(22) Filed: Feb. 22, 2012

(65) Prior Publication Data

US 2012/0236312 A1 Sep. 20, 2012

(30) Foreign Application Priority Data

Mar. 18, 2011 (JP) ................ 2011-060896

(51) Int. Cl.
| | | |
|---|---|---|
| G01N 1/20 | (2006.01) | |
| G01N 21/59 | (2006.01) | |
| G01N 21/05 | (2006.01) | |
| G01N 35/10 | (2006.01) | |
| B01L 3/00 | (2006.01) | |
| G01N 21/03 | (2006.01) | |

(52) U.S. Cl.
CPC ........... *G01N 21/05* (2013.01); *B01L 3/50825* (2013.01); *B01L 3/502715* (2013.01); *G01N 35/1095* (2013.01); *B01L 3/50273* (2013.01); *B01L 2200/141* (2013.01); *B01L 2300/0816* (2013.01); *B01L 2400/0487* (2013.01); *G01N 2021/0346* (2013.01); *G01N 2021/058* (2013.01)

(58) Field of Classification Search
CPC ............. G01N 35/1095; G01N 35/1002; G01N 2035/1004; G01N 21/05; G01N 1/14; G01N 2001/1427; G01N 2001/1436; G01N 2001/1445; G01N 2001/1454; G01N 2001/1463; G01N 2021/058; G01N 2021/0346; B01L 3/502715; B01L 3/50825; B01L 3/50273; B01L 2200/141; B01L 2200/027; B01L 2200/026; B01L 2200/0642; B01L 2200/0689; B01L 2300/0816; B01L 2400/0487

See application file for complete search history.

(56) References Cited

U.S. PATENT DOCUMENTS

| | | | | |
|---|---|---|---|---|
| 5,400,923 A | * | 3/1995 | Golias et al. ................ | 222/82 |
| 5,571,410 A | * | 11/1996 | Swedberg et al. .......... | 210/198.2 |
| 6,926,834 B2 | * | 8/2005 | Coville et al. ............... | 210/650 |
| 2008/0273918 A1 | * | 11/2008 | Linder et al. ................ | 403/31 |
| 2011/0008223 A1 | * | 1/2011 | Tsao et al. ................... | 422/502 |
| 2011/0030809 A1 | * | 2/2011 | Ying et al. .................... | 137/13 |
| 2012/0070823 A1 | * | 3/2012 | Rothmann et al. .......... | 435/6.1 |
| 2012/0216403 A1 | * | 8/2012 | Thomson et al. ........... | 29/890.09 |

FOREIGN PATENT DOCUMENTS

| | | |
|---|---|---|
| JP | 2004-271717 | 9/2004 |
| JP | 2008-008880 | 1/2008 |
| JP | 2008-064545 | 3/2008 |
| JP | 2010-133843 | 6/2010 |

* cited by examiner

*Primary Examiner* — Christopher A Hixson
(74) *Attorney, Agent, or Firm* — Chip Law Group

(57) ABSTRACT

A microchip which includes, a liquid flow path through which a liquid sample including a sample flows; and a gas flow path in which compressed gas flows, wherein liquid sample inlet which communicates with the starting end of the liquid flow path and a gas supply port which communicates with a terminal of the gas flow path are formed on the same plane, and a sealing material is disposed so as to enclose the liquid sample inlet and the gas supply port.

8 Claims, 8 Drawing Sheets

ABCUS 9,429,512 B2

MICROCHIP, LIQUID SAMPLE SUPPLY DEVICE, SUPPLY METHOD OF LIQUID SAMPLE, AND ANALYSIS DEVICE

CROSS REFERENCES TO RELATED APPLICATIONS

The present application claims priority to Japanese Priority Patent Application JP 2011-060896 filed in the Japan Patent Office on Mar. 18, 2011, the entire content of which is hereby incorporated by reference.

BACKGROUND

The present technology relates to a microchip, a liquid sample supply device in which the microchip is used, a method of supplying the liquid sample, and an analysis device. More specifically, it is related to a technology for supplying the liquid sample including a sample to a flow path which is provided in the microchip.

In recent years, a microchip has been developed in which a fine flow path or an area for performing chemical and biological analysis are formed in a substrate which is formed of an inorganic material such as silicon and glass, or a polymeric material such as plastic by applying a fine processing technology in a semiconductor field. Such a microchip has been widely used in various fields recently, such as flow cytometry or small electrochemical sensors used in medical fields, since it can perform measuring with a small sample, be manufactured at low cost, and be disposable.

In general, when performing an analysis using the microchip, a connector, a tube, and the like are connected to an opening (supply port) which is provided on the surface of the chip, and the liquid sample is introduced in the chip through these (for example, refer to Japanese Unexamined Patent Application Publication No. 2004-271717). In such a supply method in the related art, it is possible to prevent dust or the like from being mixed in the liquid sample by providing a diffusion mechanism for preventing precipitation in a vessel to which the liquid sample is input, and by disposing a filter in the middle of the tube, or in a feed orifice. In addition, in the related art, a microchip in which a filter is embedded at a part of the flow path has also been proposed (for example, refer to Japanese Unexamined Patent Application Publication No. 2008-8880).

In addition, a method of supplying the liquid sample in which a connector or tube is not used has been proposed, as well (for example, refer to Japanese Unexamined Patent Application Publication No. 2008-64545, and Japanese Unexamined Patent Application Publication No. 2010-133843). For example, in the microchip which is described in Japanese Unexamined Patent Application Publication No. 2008-64545, it is configured such that a sample chamber for communicating with the flow path is provided, and the liquid sample is injected to the sample chamber. In addition, in a method of supplying the liquid sample which is described in Japanese Unexamined Patent Application Publication No. 2010-133843, a fine pore is provided in a vessel to which the liquid sample is input, and the liquid sample in the vessel is directly supplied into the flow path of the microchip by directly connecting the pore to the feed orifice of the liquid sample which is provided in the microchip.

SUMMARY

However, in the above described related art, there is a problem as follows. That is, in the method of supplying the liquid sample in the related art in which the connector or tube is used, there is a problem in that the liquid sample is contaminated when cleaning is not sufficient, since the connector, the tube, a vial vessel to which the liquid sample is input, or the like are cleaned and repeatedly used, even if the microchip is disposable. There is also a problem in that the operation become complicated since the cleaning operation for flowing the cleaning solution after measurement is necessary to be performed every time, in order to prevent the contamination.

On the other hand, in the method of supplying the liquid sample which is described in Japanese Unexamined Patent Application Publication No. 2008-64545, and Japanese Unexamined Patent Application Publication No. 2010-133843, it is possible to effectively prevent the contamination, since the liquid sample is directly supplied to the flow path from the vessel or the sample chamber without using the connector or tube. However, for example, in the technology described in Japanese Unexamined Patent Application Publication No. 2008-64545, there is a problem in that the manufacturing process becomes complicated, and the cost thereof is increased, since a diaphragm or the sample chamber is provided in the microchip. In contrast, in the method of supplying the liquid sample which is described in Japanese Unexamined Patent Application Publication No. 2010-133843, such a problem is not caused, since the sample chamber or the like is not provided in the microchip, however, the cost for measuring the liquid sample is increased, since it is necessary to prepare a special vessel to which a fine pore is provided at a predetermined position.

Here, in the present disclosure, it is desirable to provide a microchip, a liquid sample supply device, a supply method of liquid sample, and an analysis device in which it is not necessary to perform cleaning of liquid sample supply system, and with no risk of contamination.

According to an embodiment of the present disclosure, there is provided a microchip which includes, a liquid flow path through which a liquid sample including a sample flows; and a gas flow path through which compressed gas flows, wherein liquid sample inlet which communicates with the starting end of the liquid flow path and a gas supply port which communicates with a terminal of the gas flow path are formed on the same plane, and a sealing material is disposed so as to enclose the liquid sample inlet and the gas supply port.

The diameter of the gas supply port may be set to 1 to 500 µm, in the microchip.

The gas inlet which communicates with the starting end of the gas flow path may be formed on a surface which is different from the gas supply port, or in an area which is the same surface as the gas supply port, and is the outside of the sealing material.

According to another embodiment of the present disclosure, there is provided a liquid sample supply device which includes, the microchip; a vessel which is filled with a liquid sample including a sample, and an upper part thereof is open; a chip holding unit which holds the microchip; a rotation mechanism which rotates the chip holding unit; and a gas introduction unit which introduces compressed gas into the gas flow path of the microchip.

In the supply device, the liquid sample in the vessel may come into contact with the liquid sample inlet of the microchip by holding the microchip using the chip holding unit, and rotating the holding unit using the rotation mechanism in a state where an opening end of the vessel comes into close contact with the sealing material of the microchip.

In addition, it is possible to make compressed gas which is introduced from the gas introduction unit be supplied into the vessel by flowing through the gas flow path.

Further, it is also possible to agitate the liquid sample in the vessel which is directly connected to the microchip, by rotating the holding unit using the rotation mechanism.

According to still another embodiment of the present disclosure, there is provided a method of supplying a liquid sample which includes, causing an opening end which is provided on a top of a vessel in which a liquid sample including a sample is filled to come into close contact with a sealing material which is disposed at one surface of a microchip, and the vessel to be directly connected to the microchip; causing the liquid sample in the vessel to come into contact with a liquid sample inlet which communicates with a starting end of a liquid flow path which is formed in an area which is enclosed by the sealing material of the microchip by rotating the microchip in a state where the vessel is directly connected thereto; and supplying compressed gas into the vessel from a gas supply port which is formed in an area which communicates with a terminal of the gas flow path, and is enclosed by the sealing material of the microchip, by introducing the compressed gas into a gas inlet which is provided in the microchip and communicates with the starting end of the gas flow path.

In this supply method, the amount of the liquid sample which flows into the liquid flow path may be adjusted, by changing an introduction amount of the compressed gas.

According to still another embodiment of the present disclosure, there is provided an analysis device which includes the above described liquid sample supply device. The analysis device may further include a light irradiation unit which irradiates a sample which flows through a liquid flow path of the microchip with light, and a light detection unit which detects light which is emitted from the sample.

According to the embodiments of the present disclosure, since the vessel in which the sample liquid is filled and the microchip are connected to each other, and both of the above are disposable, it is not necessary to perform a cleaning operation of the liquid sample supply system, and further, it is possible to prevent the contamination of the liquid sample.

Additional features and advantages are described herein, and will be apparent from the following Detailed Description and the figures.

DETAILED DESCRIPTION

Hereinafter, embodiments for embodying the present disclosure will be described in detail with reference to accompanying drawings. In addition, the embodiment of the present disclosure is not limited to each embodiment described in below. Further, the description will be made according to the order in below.

1. First embodiment
(an example of a microchip which is used by being directly connected with a vessel)
2. First modified example according to first embodiment
(an example of a microchip in which a gas inlet is provided on the side surface)
3. Second modified example according to first embodiment
(an example of a microchip in which the gas inlet and a liquid sample inlet are provided on the same surface)
4. Second embodiment
(an example of a device which supplies a liquid sample by directly connecting the vessel and the microchip)
5. Third embodiment
(an example of an optical measuring device including a liquid sample supply device)

1. First Embodiment

Figure 1A:
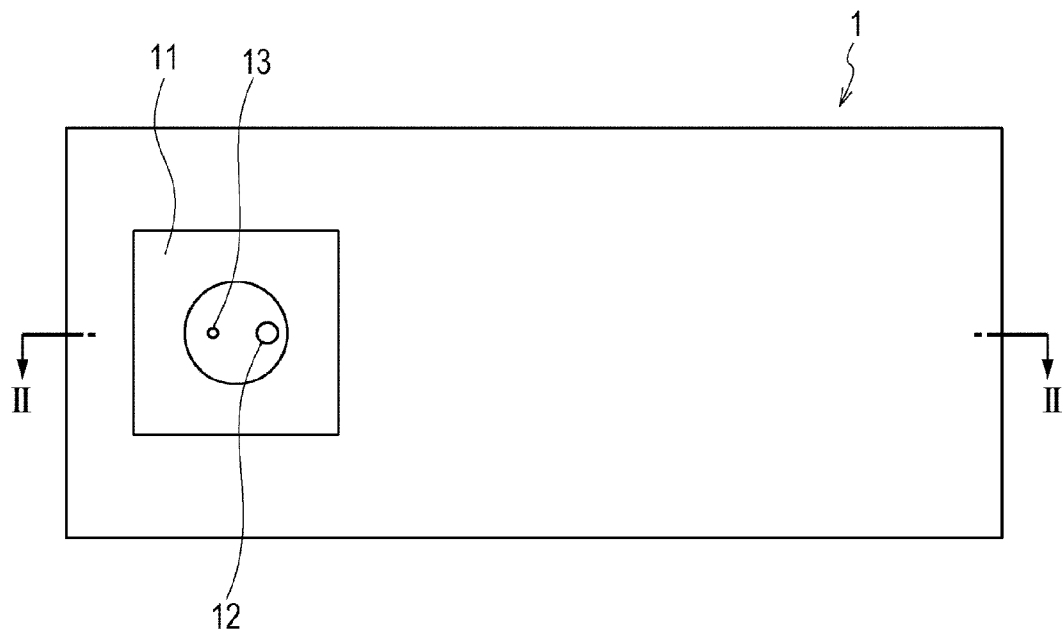
FIG. 1A is a plan view which schematically shows a structure of a microchip according to a first embodiment of the present disclosure.
Figure 1B:
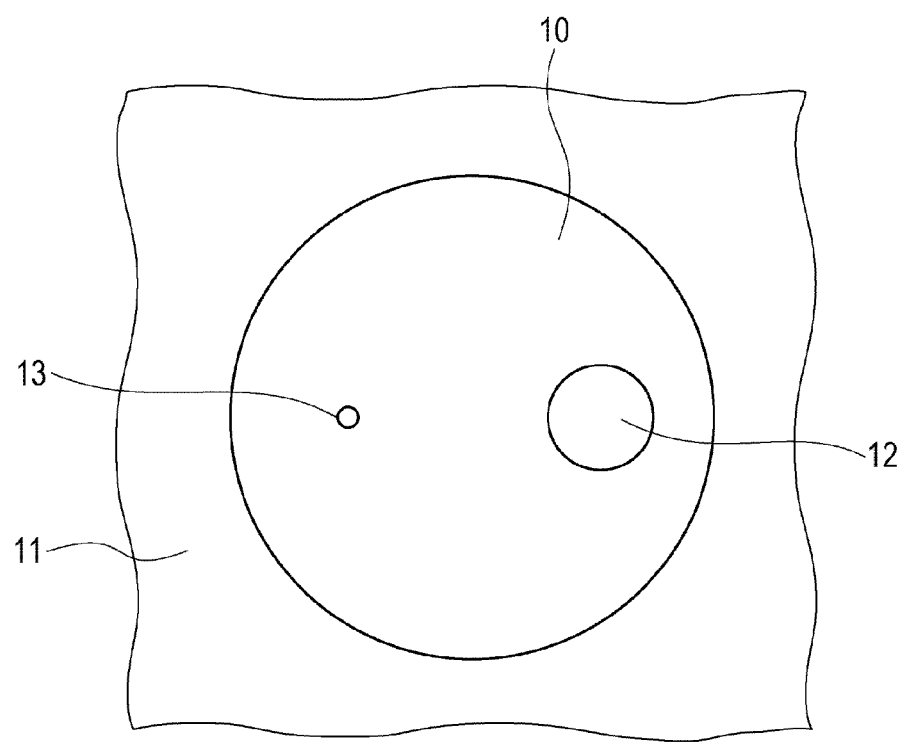
FIG. 1B is an enlarged plan view of a part of the microchip shown in FIG. 1A to which a vial is connected.
Figure 2:
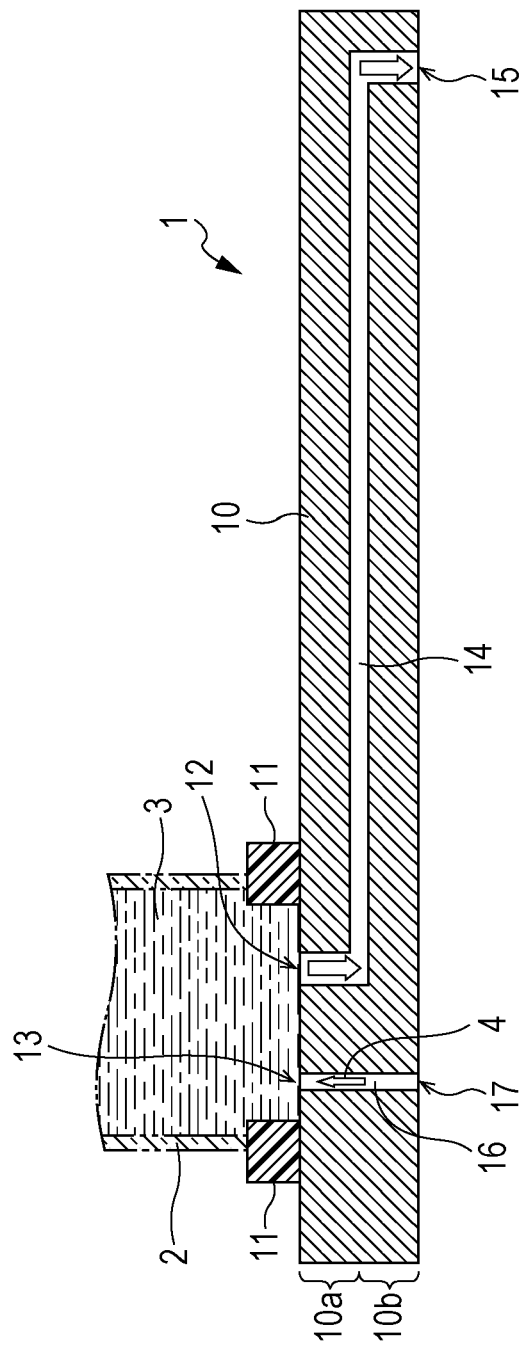
FIG. 2 is a cross-sectional view which is taken along line II-II in FIG. 1A.

First, a microchip according to a first embodiment of the present disclosure will be described. FIG. 1A is a plan view which schematically shows a structure of the microchip according to the embodiment. In addition, FIG. 1B is an enlarged plan view of a part to which a vial of the microchip 1 shown in FIG. 1A is connected. FIG. 2 is a cross-sectional view which is taken along line II-II in FIG. 1A.

Liquid Flow Path 14

As shown in FIGS. 1A to 2, at least a liquid flow path 14 through which a liquid sample 3 including a sample flows is formed on a substrate 10 of the microchip 1. The starting end of the liquid flow path 14 communicates with a liquid sample inlet 12 into which the liquid sample 3 is introduced, and a terminal of the liquid flow path 14 communicates with a drainage outlet 15 for discharging liquid which is analyzed. In addition, the diameter of the liquid flow path is not particularly limited, and can be appropriately set according to the size of the sample as the measurement target.

In addition, the number of the liquid flow path 14 is not limited to one, and a plurality of liquid flow paths may be formed in the substrate 10. Specifically, the liquid sample inlet 12 may communicate with the plurality of liquid flow paths, or the liquid flow paths which communicate with the liquid sample inlet 12 may be branched in plural. In addition, it may have a configuration in which another liquid flow path for causing liquid other than the liquid sample 3 to flow through is provided, and the liquid flow path joins the liquid flow path 14 to which the liquid sample 3 is introduced.

Gas Flow Path 16

In addition, a fine gas flow path 16 through which compressed gas flows is formed on the substrate 10 of the microchip 1. The starting end of the gas flow path 16 communicates with a gas inlet 17 to which the compressed gas 4 is introduced from outside, and a terminal thereof communicates with a gas supply port 13 for introducing gas to be transferred by being pressurized into the vessel (for example, the vial 2) into which the liquid sample 3 is filled.

The diameter of the gas flow path 16 (gas supply port 13) may be a size through which the liquid sample 3 is not able to pass under the atmospheric conditions, and may be appropriately set according to the viscosity or the like of the liquid sample 3. In general, the diameter of the gas flow path 16 (gas supply port 13) is preferably set to 1 to 500 μm, and more preferably set to equal to or smaller than 50 μm. In this manner, it is possible to supply the compressed gas 4 into the vial 2 effectively, while preventing the liquid sample 3 from flowing therein.

In addition, surface processing such as a water repellent treatment may be performed on the gas supply port 13 and at the periphery thereof, and due to this, it is possible to improve an inflow prevention effect of the liquid sample 3. Further, the shape of the gas flow path 16 (gas supply port 13) is not limited to a circular shape when planarly viewed, and may be an oval shape, a rectangular shape, a square, or a polygonal shape other than that.

Substrate 10

The substrate 10 which includes the above described liquid flow path 14 and the gas flow path 16 is formed of, for example, an upper substrate 10a and the lower substrate 10b by performing injection molding using single-sided die, accordingly, it is possible to be manufactured easily by bonding these together. At this time, as a material for forming the substrate 10, for example, there are polycarbonate, cyclo-olefin polymer, polypropylene, PDMS (polydimethylsiloxane), glass, silicon, and the like. Particularly, the substrate is preferably formed of a polymeric material such as polycarbonate, cyclo-olefin polymer, polypropylene, since they have excellent workability, accordingly, it is possible to duplicate the substrate at low cost using molding equipment.

Sealing Material 11

Further, the liquid sample inlet 12 and the gas supply port 13 are provided in the microchip 1 at positions adjacent to each other on the same surface, and a sealing material 11 such as an O-ring is disposed so as to enclose these. That is, the liquid sample inlet 12 and the gas supply port 13 are provided at a portion where the substrate 10 in the sealing material 11 is exposed.

In addition, when performing a measurement, an opening edge of the vial 2 in which the liquid sample 3 is filled comes into close contact with the sealing material 11, and the vial 2 is directly connected to the microchip 1. In this manner, the liquid sample inlet 12 and the gas supply port 13 come into contact with the liquid sample 3 in the vial 2, and a leakage of the liquid sample 3 from the connection unit of the microchip 1 and the vial 2 is prevented by the sealing material 11.

In addition, the material of the sealing material 11 is not particularly limited, however, it is possible to adopt a material which is generally used in the O-ring, or a packing, for example, such as nitrile rubber, fluororubber, acrylic rubber, ethylene propylene rubber, silicon rubber, chloroprene rubber, isobutylene-isoprene rubber, styrene-butadiene rubber, and urethane rubber, or the like.

As described above, in the microchip 1 according to the embodiment, since it is possible to directly connect the vial 2 to the microchip 1, it is possible to supply the liquid sample 3 which is filled in the vial 2 into the liquid flow path 14 which is provided in the microchip 1 without using the connector, tube, or the like. In this manner, it is possible to prevent the liquid sample 3 from precipitating during transferring.

In addition, in the microchip 1 according to the embodiment, it is possible to use a commercial vessel (vial), since the gas flow path 16 is provided in the chip, and it is configured such that compressed gas 4 is supplied into the vial 2 from the gas flow path. Due to this, it is possible to realize a disposable microchip system at low cost, and to prevent the contamination of the liquid sample 3.

In addition, the microchip according to the embodiment is preferable for an analysis and/or fractionation of biological microparticles such as cells, microorganisms, and macromolecular substances, various synthetic microparticles, and the like, and for example, may be applied to flow cytometry equipment, polymerase chain reaction (PCR) equipment, bead assay system, or the like.

2. First Modified Example According to First Embodiment

Figure 3:
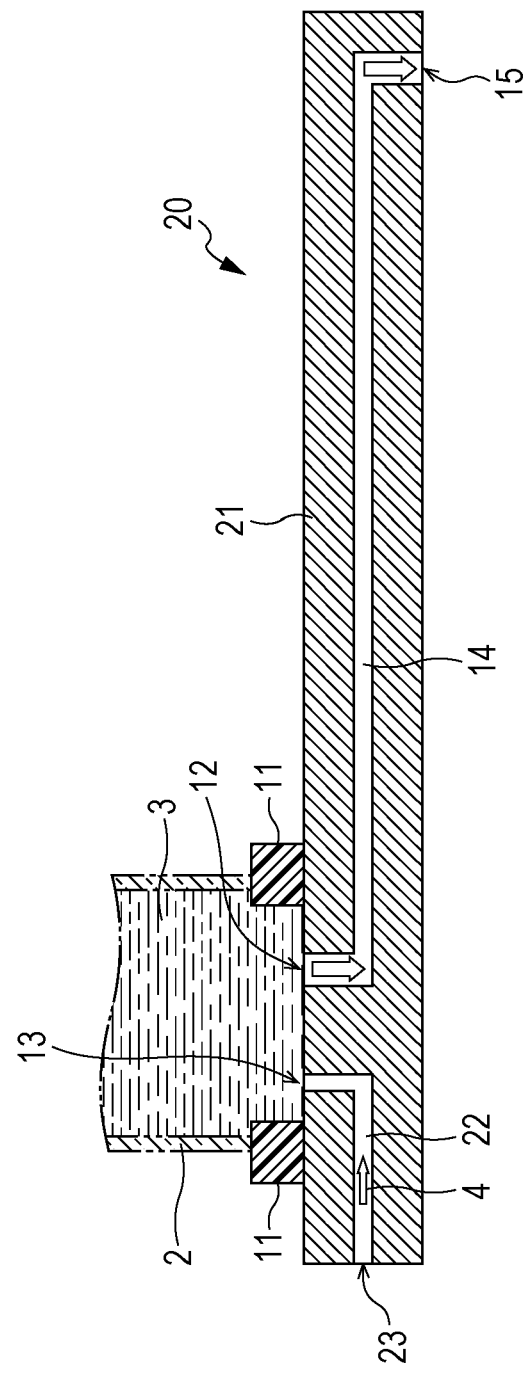
FIG. 3 is a cross-sectional view which schematically shows a structure of a microchip according to a first modified example of the first embodiment of the present disclosure.

Subsequently, a microchip according to a first modified example of the first embodiment of the present disclosure will be described. FIG. 3 is a cross-sectional view which schematically shows a structure of a microchip in the modified example. In addition, in FIG. 3, the same reference numerals are given to the same constitutional elements as that of the microchip 1 shown in FIG. 2, and detailed descriptions thereof will be omitted.

In the above described microchip 1 according to the first embodiment, the gas flow path 16 is formed so as to penetrate the substrate 10 in the thickness direction, however, this is not limited thereto in the embodiment of the present disclosure. Specifically, as shown in FIG. 3, a gas flow path 22 is formed in approximately an L shape, and a gas inlet 23 may be formed on the side surface of a substrate 21. In addition, a configuration and effect of a microchip 20 other than the above described configuration and effect according to the modified example are the same as those of the above described first embodiment.

3. Second Modified Example According to First Embodiment

Figure 4:
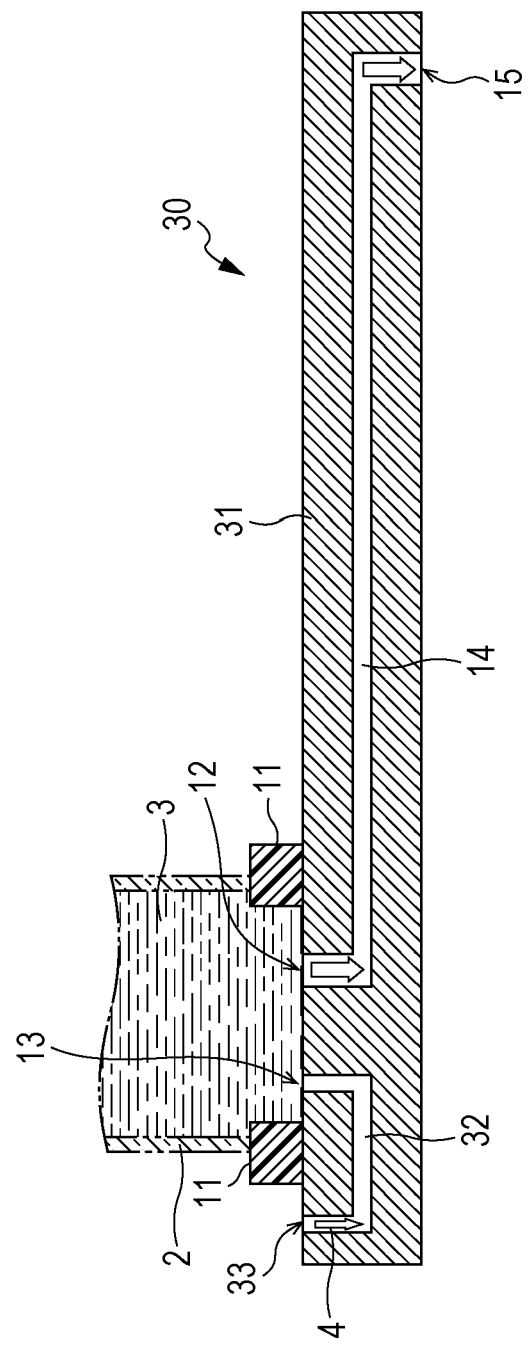
FIG. 4 is a cross-sectional view which schematically shows a structure of a microchip according to a second modified example of the first embodiment of the present disclosure.

Subsequently, the microchip according to a second modified example of the first embodiment of the present disclosure will be described. FIG. 4 is a cross-sectional view which schematically shows a structure of a microchip of a modified example. In addition, in FIG. 4, the same reference numerals are given to the same constitutional elements as those of the microchip 1 in FIG. 2, and detailed descriptions thereof will be omitted.

In addition, as shown in FIG. 4, it is also possible to form a gas flow path 32 of approximately a U shape in a substrate 31, and to form a gas inlet 33 on the same surface as a gas supply port 13, and at a position on the outer side of the sealing material 11 where the gas inlet does not come into contact with the liquid sample 3. In addition, configurations and effects other than the above described configurations and effects are the same as those of the first embodiment.

4. Second Embodiment

Subsequently, a liquid sample supply device (hereinafter, referred to simply as a supply device) according to a second embodiment of the present disclosure will be described. The liquid sample supply device according to the embodiment is a device which supplies the liquid sample to a flow path which is provided in the above described microchip of the first embodiment using a commercial vessel (vial or the like).

Configuration of Supply Device 40

Figure 5:
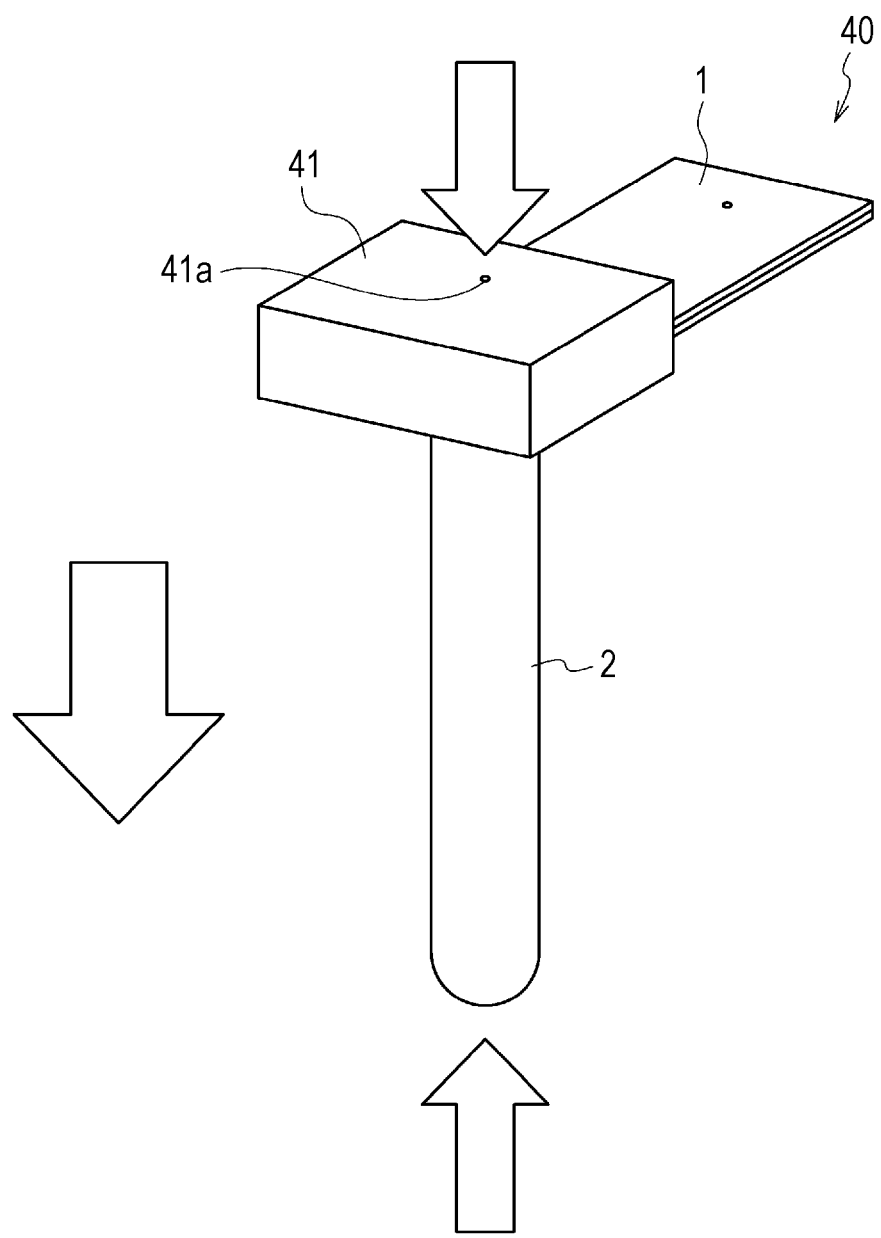
FIG. 5 is a perspective view which schematically shows a configuration of a liquid sample supply device according to a second embodiment of the present disclosure.

FIG. 5 is a perspective view which schematically shows a configuration of the supply device according to the embodiment. As shown in FIG. 5, the supply device 40 according to the embodiment includes a chip holding unit 41 which holds a microchip 1. The chip holding unit 41 is connected to a rotation mechanism (not shown), and is rotatable to an arbitrary angle, in a state of holding the microchip 1.

In addition, in the chip holding unit 41, a through hole 41a for introducing compressed gas is provided at an adjustment position to a gas inlet 17 of the microchip 1. Further, if the gas inlet 17 is covered with the chip holding unit 41 when attaching the microchip 1, the through hole 41a is not necessary.

Operation

Figure 6A:
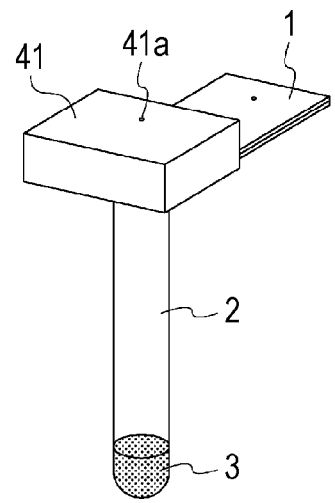
FIGS. 6A to 6C are perspective views which show operations of the liquid sample supply device shown in FIG. 5 according to order of processing thereof.
Figure 6B:
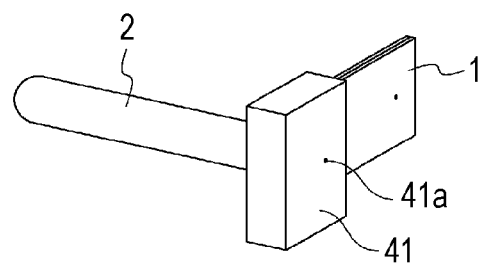
Figure 6C:
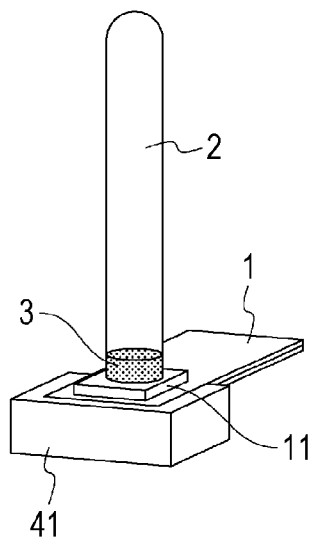

Subsequently, a method of supplying the liquid sample 3 in the vial 2 to the microchip 1 using an operation of the supply device 40 according to the embodiment, that is, using the supply device 40 will be described. FIGS. 6A to 6C are perspective views which show the operation of the supply device 40 in the order of processing. In addition, FIG. 7A is a perspective view which shows a connection state of the microchip 1 and the vial 2, and FIG. 7B is an enlarged cross-sectional view of a connection unit thereof.

First, as shown in FIG. 6A, the microchip 1 is attached to the chip holding unit 41 of the supply device 40 so that the liquid sample inlet 12 faces downward. At this time, the position of the microchip 1 is aligned so that the gas inlet 17 and the through hole 41a of the chip holding unit 41 communicate with each other. Subsequently, the liquid sample 3 is filled, and the vial 2 in a state of opening the upper surface thereof is connected to the microchip 1. Specifically, the opening end of the vial 2 is pressed to the sealing material 11 of the microchip 1, and comes into close contact with the sealing material so that the liquid sample 3 is not leaked. In addition, the vial 2 may be fixed thereto, as necessary.

Figure 7A:
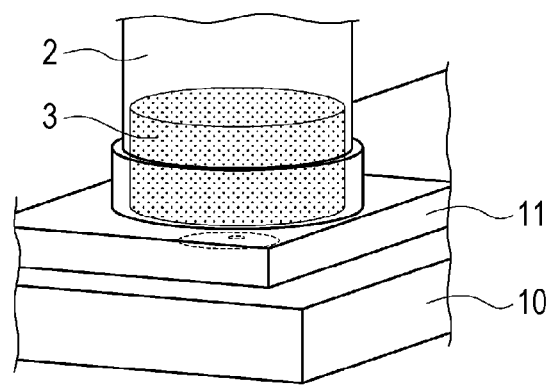
FIG. 7A is a perspective view which shows a connection state between the microchip and a vial.
Figure 7B:
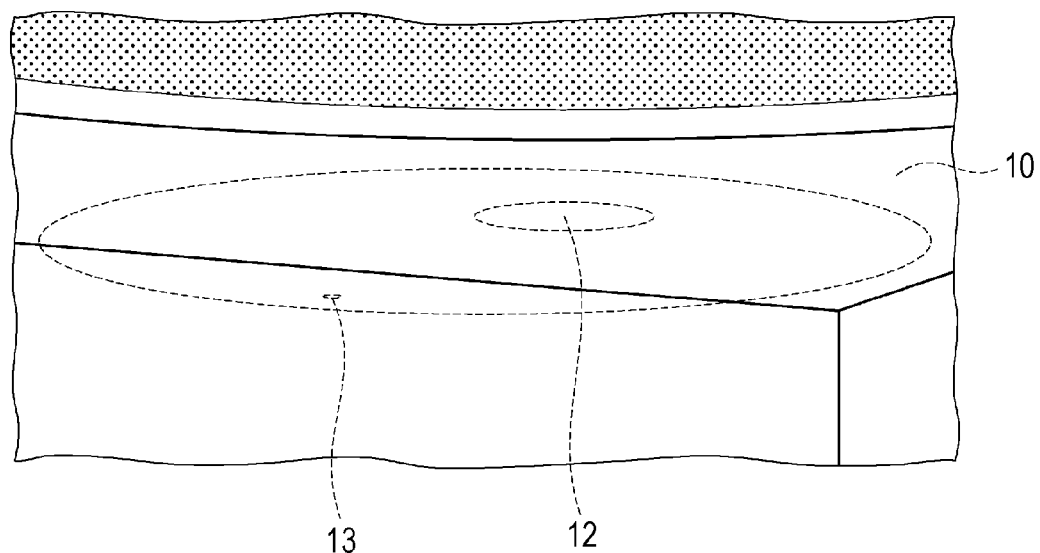
FIG. 7B is an enlarged cross-sectional view of a connection unit thereof.

Thereafter, as shown in FIGS. 6C, 7A, and 7B, the liquid sample 3 comes into contact with the liquid sample inlet 12 of the microchip 1, by rotating the chip holding unit 41 in a state where the vial 2 is connected to the microchip 1 as shown in FIG. 6B. In addition, in FIG. 6C, a case is shown where the microchip 1 is rotated by 180 degree, however, the rotation angle of the chip holding unit 41 is not particularly limited, and it may be a state where the liquid sample 3 flows into the liquid sample inlet 12. In addition, it is also possible to agitate the liquid sample 3 in the vial 2 using a rotation mechanism.

In addition, in this state, compressed gas such as compressed air is introduced from the gas inlet 17. The compressed gas is supplied into the vial 2 from the gas supply port 13 after passing through the gas flow path 16. In this manner, since the pressure in the vial 2 rises, the liquid sample 3 flows into the liquid sample inlet 12. At this time, it is possible to adjust the flow rate of the liquid sample 3 which flows through the liquid flow path 14 which is formed in the microchip 1 by changing the amount of the gas for transferring which is introduced in the gas inlet 17. In addition, the liquid sample 3 which is supplied into the microchip 1 is discharged to the outside of the chip from the discharge port 15, after being used for the analysis or the like in the liquid flow path 14.

In the liquid sample supply device 40 according to the embodiment, since the vial 2 is directly connected to the microchip 1, it is possible to supply the liquid sample 3 which is filled in the vial 2 into the liquid flow path 14 which is provided in the microchip 1, without using a connector, a tube, or the like. In this manner, it is possible to prevent the precipitation of the liquid sample 3 during transferring.

In addition, it is possible to prevent the contamination of the liquid sample 3, since the vial 2 and the microchip 1 are disposable, and accordingly, it is not necessary to perform the cleaning operation. Further, in the supply device, a pulsating flow which occurs in the related art using a liquid sending pump does not occur, since the liquid sample 3 is transferred by pressurizing the vial 2 in the inside. In addition, in the liquid sample supply device 40 according to the embodiment, it is possible to realize a disposable microchip system at low cost, since it is possible to use a vessel such as a vial, or the like in the related art.

5. Third Embodiment

Figure 8:
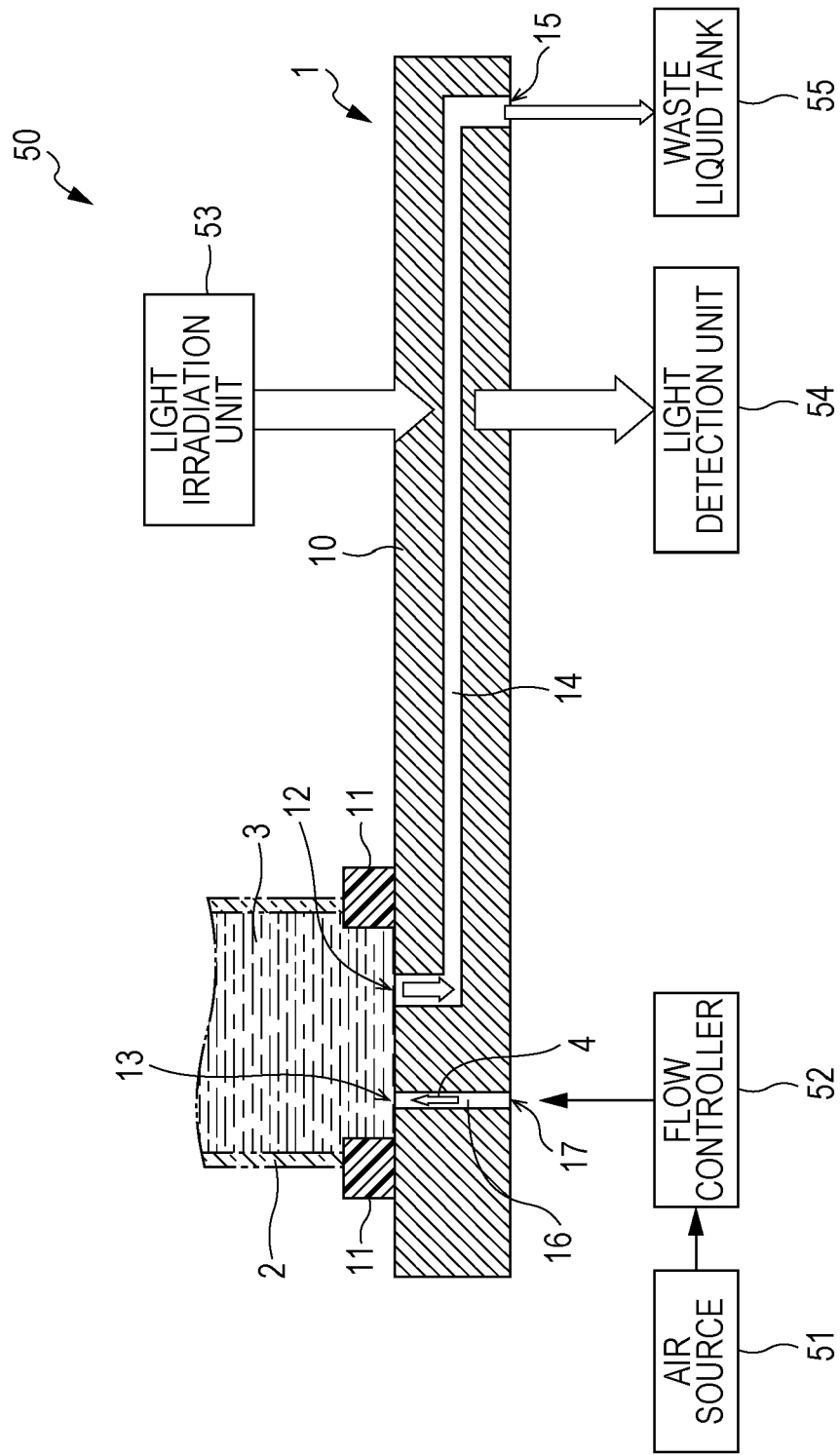
FIG. 8 is a conceptual diagram which shows a configuration of an analysis device according to a third embodiment of the present disclosure.

Subsequently, an analysis device according to a third embodiment of the present disclosure will be described using the flow cytometry. FIG. 8 is a conceptual diagram which shows a configuration of the analysis device according to the embodiment. In addition, in FIG. 8, the same constitutional elements as those of the microchip 1 in FIG. 2 will be given with the same reference numerals, and detailed descriptions thereof will be omitted.

Configuration of Analysis Device 50

In the analysis device 50 according to the embodiment supplies the liquid sample 3 to the microchip 1 using the liquid sample supply device 40 in the second embodiment, and optically analyzes a sample such as fine particles which flows through the liquid flow path 14. In addition, as shown in FIG. 8, the analysis device includes a light irradiation unit 53 such as laser which irradiates the sample as a measurement target with light, and a light detection unit 54 which has a light detector which detects light which is emitted from the sample is provided. Further, an air source 51 for introducing the compressed gas into the vial 2, and a flow controller 52 for controlling the flow rate are provided in the analysis device 50.

Operation

Subsequently, a method of analyzing the sample which is included in the liquid sample 3 using the analysis device 50 will be described. First, a vial 2 filled with the liquid sample 3 including a sample as a measurement target is directly connected to the microchip 1. In addition, for example, the liquid sample 3 filled in the vial 2 is supplied to the liquid flow path 14 of the microchip 1, using the liquid sample supply device 40 according to the above described second embodiment.

At this time, the amount of the liquid sample 3 which is introduced to the liquid flow path 14 is controlled by changing the flow rate of the compressed gas (compressed gas 14) supplied from the air source 51, using the flow controller 52. Subsequently, the liquid sample 3 which flows through the liquid flow path 14 is irradiated with light having a predetermined wavelength which is from the light irradiation unit 53, and fluorescence or scattered light which is emitted from the sample is detected by the light detection unit 54. The liquid after detecting is discharged from the discharge port 15, and is stored in a waste liquid tank 55, or the like. In addition, after finishing the measurement by causing the whole liquid sample 3 to flow through, the vial 2 and the microchip 1 are discarded.

In the analysis device 50 according to the embodiment, since the vial 2 is directly connected to the microchip 1, it is possible to supply the liquid sample 3 which is filled in the vial 2 to the liquid flow path 14 which is provided in the microchip 1 without using the connector, tube, or the like, and to perform the analyzing. In addition, since the vial 2 and the microchip 1 are disposable, it is not necessary to perform the cleaning operation. As a result, it is possible to prevent the contamination of the liquid sample 3.

In addition, in the analysis device 50 according to the embodiment, the pulsating flow as in the method in the related art using the liquid sending pump does not occur, since the liquid sample 3 is transferred by pressurizing the inside of the vial 2. Further, in the analysis device 50 according to the embodiment, it is possible to realize the disposable microchip system at low cost, since it is not necessary to prepare a dedicated vessel. In addition, configurations and effects other than the above described configurations and effects in the analysis device 50 according to the embodiment are the same as those of the above described second embodiment.

In addition, the present disclosure can be configured as follows.

(1) A microchip which includes,
a liquid flow path through which a liquid sample including a sample flows; and
a gas flow path through which compressed gas flows,
wherein liquid sample inlet which communicates with the starting end of the liquid flow path and a gas supply port which communicates with a terminal of the gas flow path are formed on the same plane, and
wherein a sealing material is disposed so as to enclose the liquid sample inlet and the gas supply port.

(2) The microchip described in (1),
wherein a diameter of the gas supply port may be set to 1 to 500 µm.

(3) The microchip described in (1) or (2),
wherein the gas inlet which communicates with the starting end of the gas flow path is formed on a surface which is different from the gas supply port.

(4) The microchip described in (1) or (2),
wherein the gas inlet which communicates with the starting end of the gas flow path is formed in an area which is the same surface as the gas supply port, and is the outside of the sealing material.

(5) A liquid sample supply device which includes, the microchip described in any one of (1) to (4);
a vessel which is filled with a liquid sample including a sample, and an upper part thereof is open;
a chip holding unit which holds the microchip;
a rotation mechanism which rotates the chip holding unit; and
a gas introduction unit which introduces compressed gas into the gas flow path of the microchip.

(6) The liquid sample supply device described in (5),
wherein the liquid sample in the vessel comes into contact with a liquid sample inlet of the microchip by holding the microchip using the chip holding unit, and rotating the holding unit using the rotation mechanism in a state where an opening end of the vessel comes into close contact with the sealing material of the microchip.

(7) The liquid sample supply device described in (5) or (6),
wherein the compressed gas which is introduced from the gas introduction unit is supplied into the vessel by flowing through the gas flow path.

(8) The liquid sample supply device described in any one of (5) to (7),
wherein the liquid sample is agitated in the vessel which is directly connected to the microchip, by rotating the holding unit using the rotation mechanism.

(9) A method of supplying a liquid sample which includes,
causing an opening end which is provided on a top of a vessel in which a liquid sample including a sample is filled to come into close contact with a sealing material which is disposed at one surface of a microchip, and the vessel to be directly connected to the microchip;
causing the liquid sample in the vessel to come into contact with a liquid sample inlet which communicates with a starting end of a liquid flow path which is formed in an area which is enclosed by the sealing material of the microchip by rotating the microchip in a state where the vessel is directly connected thereto; and
supplying compressed gas into the vessel from a gas supply port which is formed in an area which communicates with a terminal of the gas flow path, and is enclosed by the sealing material of the microchip, by introducing the compressed gas into a gas inlet which is provided in the microchip and communicates with the starting end of the gas flow path.

(10) The method of supplying a liquid sample described in (9),
wherein the amount of the liquid sample which flows into the liquid flow path is adjusted, by changing an introduction amount of the compressed gas.

(11) An analysis device which includes the liquid sample supply device which is described in any one of (5) to (8).

(12) The analysis device described in (11) which includes,
a light irradiation unit which irradiates a sample which flows through the liquid flow path of the microchip with light; and
a light detection unit which detects light which is emitted from the sample.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A liquid sample supply device comprising:
a vessel configured to be filled with a liquid sample; and
a microchip, wherein the microchip comprises:
  a liquid flow path through which the liquid sample flows; and
  a gas flow path through which compressed gas flows,
  wherein a liquid sample inlet which communicates with the liquid flow path and a gas supply port which communicates with the gas flow path are formed on a same surface of the microchip, and
  wherein the microchip is configured to be sealed with an open end of the vessel.

2. The liquid sample supply device according to claim 1, wherein the microchip is configured to be rotated to a state where the open end of the vessel comes in contact with a sealing material disposed on the surface of the microchip.

3. The liquid sample supply device according to claim 1, wherein the gas flow path is configured to supply the compressed gas into the vessel.

4. The liquid sample supply device according to claim 1, wherein the microchip is configured to be rotated so as to agitate the liquid sample filled in the vessel.

5. A method of supplying a liquid sample comprising:
causing an opening end which is provided on a top of a vessel in which a liquid sample including a sample is filled to come into close contact with a sealing material which is disposed at one surface of a microchip, and the vessel to be directly connected to the microchip;
causing the liquid sample in the vessel to come into contact with a liquid sample inlet which communicates with a starting end of a liquid flow path which is formed in an area which is enclosed by the sealing material of the microchip by rotating the microchip in a state where the vessel is directly connected thereto; and
supplying compressed gas into the vessel from a gas supply port which is formed in an area which communicates with a terminal of a gas flow path, and is enclosed by the sealing material of the microchip, by introducing the compressed gas into a gas inlet which is provided in the microchip and communicates with the starting end of the gas flow path.

6. The method of supplying a liquid sample according to claim 5, wherein an amount of the liquid sample which flows into the liquid flow path is adjusted, by changing an introduction amount of the compressed gas.

7. An analysis device comprising:
a sample supply device, wherein the sample supply device comprises:
a vessel configured to be filled with a liquid sample; and
a microchip, wherein the microchip comprises:
a liquid flow path through which the liquid sample flows; and
a gas flow path through which compressed gas flows,
wherein a liquid sample inlet which communicates with the liquid flow path and a gas supply port which communicates with the gas flow path are formed on a same surface of the microchip, and
wherein the microchip is configured to be sealed with an open end of a vessel configured to be filled with the liquid sample.

8. The analysis device according to claim 7, comprising:
a laser configured to irradiate the liquid sample, which flows through the liquid flow path of the microchip, with light; and
a light detector configured to detect light which is emitted from the liquid sample.

* * * * *